United States Patent [19]

Lipowski

[11] Patent Number: 4,504,316
[45] Date of Patent: Mar. 12, 1985

[54] ALUMINUM SALTS OF AROMATIC SULFONIC ACIDS FORMALDEHYDE CONDENSATES

[75] Inventor: Stanley A. Lipowski, Livingston, N.J.

[73] Assignee: Diamond Shamrock Chemicals Company, Dallas, Tex.

[21] Appl. No.: 417,515

[22] Filed: Sep. 13, 1982

Related U.S. Application Data

[62] Division of Ser. No. 345,238, Feb. 3, 1982, Pat. No. 4,443,382.

[51] Int. Cl.³ ............................................. C04B 7/35
[52] U.S. Cl. ...................................... 106/90; 106/314
[58] Field of Search .......................... 106/90, 314, 315

[56] References Cited

U.S. PATENT DOCUMENTS 4,080,217  3/1978  Pierre et al. ..................... 106/90
4,308,069  12/1981  Tsuji et al. ....................... 106/90

Primary Examiner—James Poer
Attorney, Agent, or Firm—Leslie G. Nunn, Jr.

[57] ABSTRACT

Aluminum salts of aromatic sulfonic acid formaldehyde condensates are useful cement additives and leather retanning agents. These salts prepared by reaction of freshly precipitated aluminum hydroxide with aromatic sulfonic acid formaldehyde condensate are of higher purity than aluminum salts obtained by prior art processes.

10 Claims, No Drawings

ALUMINUM SALTS OF AROMATIC SULFONIC ACIDS FORMALDEHYDE CONDENSATES

This is a division of application Ser. No. 345,238 filed Feb. 3, 1982 now U.S. Pat. No. 4,443,382.

BACKGROUND OF THE INVENTION

1. Field of the Invention

This invention relates to an aluminum salt of an aromatic sulfonic acid formaldehyde condensate, its preparation and use.

2. Description of the Prior Art

Aluminum salts of aryl or alkylaryl sulfonic acids formaldehyde condensates are not easily prepared by reaction of sulfonic acids with aluminum oxides in the form of corundum, hydroargillite, bayerite or amorphorous $Al_2O_3 \cdot XH_2O$ or with the hydroxide $AlO(OH)$ in the form of boehmite or diaspore.

U.S. Pat. No. 4,080,217—Falcoz et al, issued Mar. 21, 1978, describes preparation of aluminum salts of calcium aryl or alkylaryl sulfonates. These aluminum salts may be prepared (1) by reaction of a solution of an aluminum aryl or alkylaryl sulfonate with a milk of lime solution; (2) by reaction of a solution of a calcium aryl or alkylaryl sulfonate on anhydrous tricalcium aluminate; or by reaction of monocalcium aluminate or a lime solution and a calcium aryl or alkylaryl sulfonate. The resulting alumino calcium compositions are useful as water reducing agents for hydraulic binders.

SUMMARY OF THE INVENTION

Aluminum salts of aromatic sulfonic acids formaldehyde condensates in higher purity than obtained with art processes are prepared by reaction of freshly precipitated aluminum hydroxide with aromatic sulfonic acid formaldehyde condensates. An effective amount of one of these aluminum salts is added to a cement or concrete mix to improve compressive strength. From about 0.1 to about 2.0% by weight of an aluminum salt based on the weight of cement present in the mix may be added. An effective amount of the aluminum salt is also used as a retanning agent on chrome tanned stock. From about 5.0 to about 15.0% by weight of an aluminum salt based on leather stock may be used.

DETAILED DESCRIPTION

Aluminum salts of aromatic sulfonic acid formaldehyde condensates can also be named as aluminum salts of aromatic formaldehyde sulfonic acids or formalin condensates of aromatic sulfonic acids or condensation products of aromatic sulfonic acids with formaldehyde. Aromatic sulfonic acid formaldehyde condensates may be prepared by reacting a mixture of an aromatic hydrocarbon such as naphthalene, sulfuric acid and formaldehyde. These condensates may be prepared by the processes described in U.S. Pat. No. 2,141,569—Tucker et al, issued Dec. 27, 1938; U.S. Pat. No. 3,193,575—Nebel et al, issued July 6, 1965 and U.S. Pat. No. 3,277,162—Johnson, issued Oct. 4, 1966. Details on analysis of these condensates may be found in U.S. Pat. No. 4,290,817—Villa et al, issued Sept. 22, 1981.

Useful aluminum salts include aluminum salts of benzene sulfonic acid formaldehyde condensates, alkylated benzene sulfonic acid formaldehyde condensates, naphthalene sulfonic acid formaldehyde condensates, alkylated naphthalene sulfonic acid formaldehyde condensates or the like. Homologs and derivatives of these aromatic sulfonic acids may also be used in the preparation of useful aluminum salts.

Aluminum salts of aromatic sulfonic acid formaldehyde condensates may be produced by reacting freshly precipitated aluminum hydroxide with the aromatic sulfonic acid formaldehyde condensate. From about 1.0 to about 1.2 moles of freshly prepared aluminum hydroxide is reacted with one mole of aromatic sulfonic acid formaldehyde condensates in aqueous solution at from about 40° to about 60° C. The resulting aqueous aluminum salt solution is evaporated to obtain the dried salt in powder form.

Freshly precipitated aluminum hydroxide may be prepared adding ammonium hydroxide to an aqueous solution of an aluminum salt such as aluminum sulfate to precipitate aluminum hydroxide, filtering off the freshly precipitated hydroxide and washing the precipitate until free of excess ammonia.

When the aluminum salts are used in cement or concrete mixes, from about 0.1 to about 2.0% by weight of the salt based on the weight of cement are present in the mix. Cement mixes may contain 100 parts by weight of cement, from about 200 to about 400 parts by weight of sand and from about 40 to about 60 parts by weight of water. Concrete mixes may contain 100 parts by weight of cement, from about 100 to about 300 parts by weight of sand, from about 100 to about 200 parts by weight of aggregates such as gravel and from about 40 to about 60 parts by weight of water.

The aluminum salt solution or its dried powder form may be added to a cement or concrete mix at any convenient point during preparation or use. For example, the dried powder may be added to portland cement clinker prior to grinding and thoroughly mixed with the cement during grinding or may also be blended with the ground cement. Either the aluminum salt solution or powder may be added to the water which is mixed with cement, sand and/or gravel. The dry powdered cement may be premixed with water and then either the aluminum salt solution or powder added. In general, either form of the salt may be added to the cement, mortar or concrete mix at any stage prior to final setting. Cement, mortar or concrete mixes include concretes, mortars, neat paste compositions, oil well cement slurries, grouting compositions and the like.

Cements may be used in the preparation of cement and concrete mixes. Cements include Type I, II and III cements. Properties of these cements are well known and are described in the Portland Cement Association Engineering Bulletin entitled, "Design and Control of Concrete Mixtures", Eleventh Edition, July 1968, and "Kirk-Othmer Encyclopedia of Chemical Technology", Second Edition (Interscience Publishers, New York, N.Y. 1967), Volume 4, pages 690–692.

The aluminum salt solution or its dried powder form may also be used in chrome tannages of side leathers and retans on splits. When these aluminum salts are used in chrome tannages of side leather, i.e., as a retan on chrome, they give the chrome leather a soft fullness, a mellow grain and a hand which is light and warm. Replacement tanning values of these salts impart mellowness to the leather and require less fat liquor to attain the desired degree of softness. Mellowness and softness characteristics are very desirable in glove, garment and soft type leathers.

When these salts are used as replacement syntans in chrome tannages of side leather, from 1% of solids to 20% of solids by weight of the syntans based on the weight of the leather used are normally employed at a pH of from 5.0 to 3.0 and are introduced at 75° F. to 125° F. over from ½ to 8 hours. Further, these salts are particularly well suited for retanning chrome tannage splits for garments, suedes and casual upper leather suedes. Use of these salts in retanning splits improves oil distribution and eliminates bony areas. When they are applied as relatively light retans, they provide retanned splits having silky naps with pleasing hands. Usually when these salts are used as retans on splits, from 0.05% of solids to 5% of solids by weight of syntan based on the weight of leather is introduced at a pH of from 5.0 to 3.0 at from 60° F. to 120° F. over from ½ to 5 hours.

For a fuller understanding of the nature and advantages of this invention, reference may be made to the following examples. These examples are given merely to illustrate the invention and are not to be construed in a limiting sense. All quantities, proportions and percentages are by weight and all references to temperature are °C. unless otherwise indicated.

EXAMPLE I

This example describes preparation of a naphthalene sulfonic acid formaldehyde condensate outside the scope of this invention.

To 128 g (1 mole) of naphthalene was added 120 g (1.2 mole) of 98% sulfuric acid. The sulfonation mixture was then heated to 160° C. and held at this temperature for 3 hours. After heating, the mixture was cooled to 95° C. and 170 g of water and 100 g (1.23 mole) of 37% formaldehyde solution were added to obtain a condensation mixture. The condensation mixture was heated to reflux, refluxed for 30 hours, then cooled to 60° C. and treated with a suspension of 14 g lime in 30 g water. After treating with lime for 24 hours, the condensation mixture was filtered to remove precipitated calcium sulfate. The filtered solution of the condensation mixture contained 42% solids as naphthalene sulfonic acid formaldehyde condensate and had an acid value of 10.9% sulfuric acid.

EXAMPLE II

This example describes preparation of the aluminum salt of a naphthalene sulfonic acid which is within the scope of this invention.

135 g of $Al_2(SO_4)_3.17H_2O$ was dissolved in 1350 grams water and 110 g of ammonium hydroxide water solution containing 28% ammonia added. The white, slightly gelatinous precipitate of aluminum hydroxide was filtered and washed until free of excess ammonia. The solution of the naphthalene sulfonic acid formaldehyde condensate prepared in Example I was then heated to about 40°–45° C. and the slurry of the aluminum hydroxide was slowly added to condensate solution under good agitation until the pH reached 3.2 to obtain a solution of the aluminum salt. The solution of the aluminum salt was then filtered and the solution dried in vacuum. The dried aluminum salt was a light tan colored powder which was a pure aluminum salt of the naphthalene sulfonic acid formaldehyde condensate representing a 100% conversion of the acid to its aluminum salt.

EXAMPLE III

This example describes preparation of an aluminum salt according to U.S. Pat. No. 4,080,217, column 3, which is outside the scope of this invention.

A charge of 64 g (0.5 mole) of naphthalene was heated to 160° C. and 75 g (0.75–0.765 mole) of 98–100% strength sulfuric acid was added. The reaction mixture was maintained for 2 hours at 160° C. under constant stirring, was then cooled to 100° C. and 20 g of water added. Then 40 g of 37% by weight formaldehyde solution and 80 g of water were added and the reaction mixture maintained at 100° C. for 4 hours to obtain a naphthalene sulfonic acid formaldehyde condensate solution. The condensate solution was added to a milk of lime mixture containing 37 g of lime and 56 g water, to which was then added 166 g of crystalline aluminum sulfate dissolved in 300 grams of water. Calcium sulfate was filtered off and a 20% by weight solution of the aluminum salt of the naphthalene sulfonic acid formaldehyde condensate obtained.

After drying of the aluminum salt, it was found that less than 70% of the naphthalene sulfonic acid formaldehyde condensate was converted to the aluminum salt.

EXAMPLE IV

This example describes preparation of an alkylbenzene sulfonic acid formaldehyde condensate outside the scope of this invention.

To 200 g of an alkylbenzene containing a side chain of $C_{10}$–$C_{14}$ hydrocarbons were added 400 grams of 100% sulfuric acid. Temperature of the reaction mixture rose from 24° C. to 33° C. Low heat was applied and the temperature was raised to 48° C. A high exotherm started and it was controlled by ice-water cooling. The maximum temperature was 65° C. After the exothermic reaction subsided, the reaction mass was kept at 65° C. for 2 hours. A sample of the product was clearly soluble in cold water. The reaction mixture was then cooled to 20° C. and 100 g ice were added and stirred for 30 minutes. The resulting mixture was transferred to a separatory funnel and allowed to stand overnight for phase separation. On the following day the bottom layer (spent acid) was drained. The upper layer, about 300 g of alkylbenzene sulfonic acid was transferred to a reaction flask where 158 g water and 63 g formaldehyde 37% by weight solution were added slowly and mixed to obtain a uniform solution. The solution was heated gradually to 100° C. and held at 100° C. for 20 hours. The resulting brown, viscous solution was the alkylbenzene sulfonic acid formaldehyde condensate.

EXAMPLE V

This example describes preparation of an aluminum salt of an alkylbenzene sulfonic acid formaldehyde condensate which is within the scope of this invention.

The alkylbenzene sulfonic acid formaldehyde condensate prepared in Example IV was diluted with 100 g water and then neutralized at 60°–65° C. with freshly prepared aluminum hydroxide as in Example II to a final pH of 3.0. The reaction mixture separated into a upper layer which was the aluminum salt and a bottom layer which was water. After transfer to a separatory funnel, the bottom layer was drained off and the top layer was transferred to a porcelain dish and dried in vacuum. The dried aluminum salt of the condensate was a brown, slightly sticky solid, soluble in alcohol, acetone, kerosene and mineral oil.

EXAMPLE VI

This example describes evaluation of an aluminum salt of a naphthalene sulfonic acid formaldehyde condensate in cement casting mixes. A cement casting mix was prepared using 800 parts by weight of cement, 2400 parts by weight of sand and 370 parts by weight of water. The casting mixture was agitated for 3 minutes, allowed to stand for 3 minutes and then mixed for an additional 2 minutes. This casting mixture was designated as Blank No. 1.

The same casting mix was prepared with the only difference being that 4 parts by weight of additive based on dry basis was added to the water for the casting mix. Two additives were used, one additive was a commercial sodium salt of a naphthalene sulfonic acid formaldehyde condensate in form of a 40% water solution designated below as Sodium salt and the other was the aluminum salt of the condensate prepared in Example II designated below as Aluminum salt.

A second cement casting mix was prepared using 770 parts by weight of cement, 1510 parts by weight of sand, 1150 parts by weight of aggregates and 385 parts by weight of water. This casting mix was designated as Blank No. 2.

The two additives, Sodium salt and Aluminum salt, were added at the same concentrations to the water used in the second casting mix.

Slump for both casting mixes was measured according to ASTM standard C143-74. Air content was checked with a Chaser air indicator. Specimens used in compressive strength testing were 3×6 inch cylinders, consolidated by rodding and cured at 21°-24° C. and at 100% relative humidity. Data were collected based on the average from three cylinders following ASTM standard C39-72 after 1, 7 and 28 days.

Results of tests with these two different additives and two cement mixtures are summarized in Tables I and II below.

TABLE I

| Additive | % Air Content | Slump (inches) | Compressive Strength (psi) 1 day | 7 days | 28 days |
|---|---|---|---|---|---|
| Blank No. 1 | 3.2 | 2¼ | 1600 | 2650 | 3380 |
| Sodium salt | 5.0 | 1⅞ | 2100 | 3500 | 4450 |
| Aluminum salt | 4.0 | 1¼ | 2470 | 4100 | 5230 |

TABLE II

| Additive | % Air Content | Slump (inches) | Compressive Strength (psi) 1 day | 7 days | 28 days |
|---|---|---|---|---|---|
| Blank No. 2 | 4.5 | 5¾ | 1930 | 3500 | 4460 |
| Sodium salt | 4.0 | 7¼ | 3100 | 4300 | 5800 |
| Aluminum salt | 4.0 | 6.0 | 3500 | 5300 | 6600 |

EXAMPLE VII

This example describes evaluation of an aluminum salt of a naphthalene sulfonic acid formaldehyde condensate as a retanning agent for straight chrome tanned leathers versus a commercial sodium salt of a naphthalene sulfonic acid formaldehyde condensate.

The salts were evaluated on Ocean Leathers Company straight chrome tanned stock.

First, a 7% dispersion of the aluminum salt of the condensate from Example II designated as Aluminum salt was prepared by adding sufficient sodium hydroxide to attain a pH of 8.3. At this level of alkalinity, a dispersion was attained that showed excellent stability at 100° F. No separation noted after 1 hour standing. The commercial sodium salt of the condensate was designated as Sodium salt.

The Aluminum salt and Sodium salt were applied to leather. Two control applications were conducted:
(1) Sodium salt (7% solution pH—9.4).
(2) Sodium salt—pH modified (7% solution pH—8.3).

Leather Application:
Stock—Ocean Leather Company—4½ ounces single gauge weight.

| Test | Leather Punch | Stock Weight | Application |
|---|---|---|---|
| 1 | 0 | 290 grams | 7% Sodium salt (pH 9.4); 5% Commercial fat liquor |
| 2 | 00 | 318 grams | 7% Sodium salt (pH 8.3). 5% Commercial fat liquor |
| 3 | 000 | 325 grams | 7% Aluminum salt (pH 8.3); 5% Commercial fat liquor |

1. Washed leathers using 300% float at 100° F. Ran 30 minutes, drained (pH 3.7).
2. Added 7% Sodium salt or Aluminum salt/100% float/100° F. Ran 45 minutes. pH (1) 5.4; (2) 4.7; (3) 5.3.
3. To Test 1—Added 0.33% formic acid/diluted. Ran 60 minutes, pH 4.6.
To Test 2—Added 0.67% formic acid/diluted/—2 feeds—15 min/45 minutes, pH 3.8.
To Test 3—added 1.33% formic acid/diluted/—4 feeds—15 minutes/15 minutes/15 minutes/15 minutes; pH 3.8.
4. Drained, washed all tests 10 minutes at 120° F., 5 minutes; drained.
5. To all tests, added 5% commercial fat liquor/100% float/120° F. Ran 60 minutes (oil takeups only fair for Tests 1 and 2, good but not complete for Test 3).
6. To all tests, added 0.33% formic acid/diluted. Ran 15 minutes. Pulled leathers, horsed to drum overnight. (Exhausts all satisfactory, pH (1) 3.8; (2) 3.8; (3) 3.9.

After overnight horse, the leathers were tacked out to dry in a 50° C. oven for 4½ hours. Leathers were stripped from the boards and allowed to mull (lay over) overnight.

Leather Evaluation:

Test 1 and 2 Controls

Identical. Typical for Sodium salt retannage—leathers very firm and boardy. Degree of bleach marginal—blue white tone. 72 hour UV sunlamp exposures yielded equal degree of yellowing.

Test 6 Leather

Much softer than control applications. Degree of leather fullness, tightness of grain break, grain layout, bleach and UV resistance equivalent to control leathers.

While the invention has been described with reference to certain specific embodiments thereof, it is understood that it is not to be so limited since alterations and changes may be made therein which are within the full and intended scope of the appended claims.

What is claimed is:

1. In a process for producing a hardened cement mix having enhanced compressive strength comprising adding an amount effective to improve compressive strength of the hardened cement mix of an aluminum salt of an aromatic sulfonic acid formaldehyde condensate wherein the aluminum salt is a reaction product of an aromatic sulfonic acid formaldehyde condensate with freshly prepared aluminum hydroxide to a cement mix containing 100 parts by weight of cement, from about 200 to about 400 parts by weight of sand and from about 40 to about 60 parts by weight of water.

2. The process of claim 1 wherein the aluminum salt is a reaction product of one mole of an aromatic sulfonic acid formaldehyde condensate with from about 1.0 to about 1.2 mole of freshly prepared aluminum hydroxide.

3. The process of claim 1 wherein the aromatic sulfonic acid is naphthalene sulfonic acid.

4. The process of claim 1 wherein the aromatic sulfonic acid is alkylbenzenesulfonic acid.

5. Hardened cement produced by the process of claim 1.

6. In a process for producing a hardened concrete mix having enhanced compressive strength comprising adding an amount effective to improve compressive strength of the hardened concrete mix of an aluminum salt of an aromatic sulfonic acid formldehyde condensate wherein the aluminum salt is a reaction product of an aromatic sulfonic acid formaldehyde condensate with freshly prepared aluminum hydroxide to a concrete mix containing 100 parts by weight of cement, from about 100 to about 300 parts by weight of sand, from about 100 to about 200 parts by weight of aggregate and from about 40 to about 60 parts by weight of water.

7. The process of claim 6 wherein the aluminum salt is a reaction product of one mole of an aromatic sulfonic acid formaldehyde condensate with from about 1.0 to about 1.2 mole of freshly prepared aluminum hydroxide.

8. The process of claim 6 wherein the aromatic sulfonic acid is naphthalene sulfonic acid.

9. The process of claim 6 wherein the aromatic sulfonic acid is alkylbenzenesulfonic acid.

10. Hardened concrete produced by the process of claim 6.

* * * * *